(12) United States Patent
Cheng et al.

(10) Patent No.: US 9,999,287 B2
(45) Date of Patent: Jun. 19, 2018

(54) PACKAGING CONTAINER WITH SMEARING COMPONENT

(71) Applicant: SHENZHEN BEAUTY STAR CO., LTD, Shenzhen, Guangdong (CN)

(72) Inventors: Ruofei Cheng, Guangdong (CN); Shenzhou Li, Guangdong (CN); Zhu Bao, Guangdong (CN)

(73) Assignee: SHENZHEN BEAUTY STAR CO., LTD, Shenzhen (CN)

( * ) Notice: Subject to any disclaimer, the term of this patent is extended or adjusted under 35 U.S.C. 154(b) by 125 days.

(21) Appl. No.: 15/069,995

(22) Filed: Mar. 15, 2016

(65) Prior Publication Data

US 2016/0192763 A1 Jul. 7, 2016

Related U.S. Application Data

(63) Continuation of application No. PCT/CN2015/072820, filed on Feb. 12, 2015.

(30) Foreign Application Priority Data

Oct. 24, 2014 (CN) .......................... 2014 1 0579247

(51) Int. Cl.
*A45D 40/26* (2006.01)
*A45D 34/04* (2006.01)
*B65D 47/42* (2006.01)
*A61M 35/00* (2006.01)

(52) U.S. Cl.
CPC ........... *A45D 40/262* (2013.01); *A45D 34/04* (2013.01); *A61M 35/003* (2013.01); *B65D 47/42* (2013.01)

(58) Field of Classification Search
CPC ........ A45D 40/28; A45D 40/26; A45D 40/10; A45D 40/00; A45D 40/262; B43M 11/06; B43K 5/00; A61Q 1/02
See application file for complete search history.

(56) References Cited

U.S. PATENT DOCUMENTS

| | | | | |
|---|---|---|---|---|
| 3,495,858 A * | 2/1970 | Kindel | ................ | F16C 11/0633 403/140 |
| 4,648,732 A * | 3/1987 | Smialkowski | ......... | B65D 47/42 401/196 |
| 6,592,282 B2 * | 7/2003 | Fontanet | ................ | A45D 34/04 401/188 R |
| 6,795,562 B1 * | 9/2004 | Gunnersen | ........... | H04R 25/654 381/322 |

(Continued)

*Primary Examiner* — David Walczak (57) ABSTRACT

The present invention relates to a packaging container with a smearing component, which includes a container body, a smearing component, a sealing cap and a buckle. The sealing cap engages with the container body and the container body is entirely sealed by the sealing cap. The smearing component is rotatably arranged around an opening end of the container body. A part of the buckle plug is fixed on the container body, the other part thereof matches with an end of the smearing component, and the smearing component is positioned in an axial direction by the buckle plug and the container body. The advantages of the packaging container can be achieved by the smearing component being arranged on a rolling rod of the liquid outlet of the container body and the smearing component being positioned on the container body in the axial direction by means of the buckle plug.

19 Claims, 8 Drawing Sheets (56) References Cited

U.S. PATENT DOCUMENTS

| | | | | |
|---|---|---|---|---|
| 7,309,184 B2* | 12/2007 | Butcher | ............ | A45D 34/04 |
| | | | | 401/172 |
| 8,065,774 B2* | 11/2011 | Schiesz | ............ | A46B 5/0075 |
| | | | | 15/143.1 |
| 8,602,671 B2* | 12/2013 | Kim | ............ | A45D 34/041 |
| | | | | 401/208 |
| 9,138,045 B2* | 9/2015 | Habibi-Naini | ............ | A46B 11/00 |
| 9,386,839 B2* | 7/2016 | Bonnin | ............ | A45D 34/04 |
| 9,504,305 B2* | 11/2016 | Jung | ............ | A45D 40/26 |
| 2006/0285913 A1* | 12/2006 | Koptis | ............ | A45D 40/26 |
| | | | | 401/205 |
| 2007/0157406 A1* | 7/2007 | Kim | ............ | A46B 5/0075 |
| | | | | 15/172 |
| 2007/0217860 A1* | 9/2007 | Byun | ............ | B65D 35/36 |
| | | | | 401/205 |
| 2008/0279616 A1* | 11/2008 | Thorpe | ............ | A45D 34/04 |
| | | | | 401/265 |
| 2010/0034574 A1* | 2/2010 | Zhang | ............ | A45D 40/24 |
| | | | | 401/47 |
| 2011/0250008 A1* | 10/2011 | Lim | ............ | A45D 40/261 |
| | | | | 401/188 R |
| 2014/0023425 A1* | 1/2014 | Bonnin | ............ | A45D 34/04 |
| | | | | 401/265 |
| 2014/0161504 A1* | 6/2014 | Duquet | ............ | A45D 34/04 |
| | | | | 401/147 |
| 2015/0101630 A1* | 4/2015 | Kodama | ............ | A45D 19/02 |
| | | | | 132/200 |
| 2015/0257511 A1* | 9/2015 | Maurin | ............ | A45D 34/04 |
| | | | | 401/118 |
| 2015/0296957 A1* | 10/2015 | Megaro | ............ | A45D 34/041 |
| | | | | 132/200 |
| 2016/0029770 A1* | 2/2016 | Megaro | ............ | A45D 34/041 |
| | | | | 401/220 |

* cited by examiner

PACKAGING CONTAINER WITH SMEARING COMPONENT

CROSS REFERENCE TO RELATED APPLICATIONS

The present application is a Continuation Application of PCT application No. PCT/CN2015/072820 filed on Feb. 12, 2015, which claims the benefit of Chinese Patent Application No. 201410579247.3 filed on Oct. 24, 2014. All the above are hereby incorporated by reference.

BACKGROUND OF THE INVENTION

Technical Field

The present invention relates to packaging field, and more particularly, to a packaging container with a smearing component.

Description of Related Art

Smearing components can be used in many fields, for example, in medicine field the smearing component can assist a user to smear ointment on parts of one's body, in cosmetic field the smearing component can assist a user to smear lipstick and lip balm on lips, to smear moisturizer, eye cream and different liquid essence on parts of one's body which need to be cared. In current technology, the smearing components of the packages of cosmetics and medicines are generally fixed on headers of the packages, the smearing components can't be rotated, the dissolved contents in the smearing components can't be smeared evenly so that a hand is needed to smear the dissolved contents, it is not healthy to use a hand, and the smearing can't be completed by using the smearing component directly.

SUMMARY OF THE INVENTION

A technical problem to be solved by the present invention is to provide a packaging container with a smearing component, and the packaging container has a simple structure, can smear the dissolved contents on parts of a body evenly.

In order to solve above technical problem, the present invention provides a packaging container with a smearing component including a container body, a smearing component, a sealing cap and a buckle plug, the sealing cap being engaged with the container body and the container body being entirely sealed by the sealing cap, wherein the smearing component is rotatably arranged around an opening end of the container body in a radial direction, a part of the buckle plug is fixed on the container body, the other part of the buckle matches with an end of the smearing component, and the smearing component is positioned in an axial direction by the buckle plug and the container body.

Furthermore, the opening end of the container body includes a cylindrical rolling rod, a free end of the rolling rod is provided with a liquid outlet internally communicated with the container body, a rolling hole is arranged inside the smearing component, and the rolling hole is arranged outside and around the rolling rod by matching thereof, the buckle plug includes a cock body and a press cover, the cock body is extended into the liquid outlet of the rolling rod and engages with the rolling rod tightly, the press cover engages with an end of the smearing component to prevent movement of the smearing component on the rolling rod in an axial direction.

Furthermore, the buckle plug is provided with a channel for discharging liquid between the container body and outside, the channel includes a through-hole in the cock body in an axial direction and an opening provided at the middle of the press cover, the opening communicates with the through-hole of the cock body.

Furthermore, the container body further includes a receiving section and a joint section, the receiving section, the joint section and the rolling rod are arranged in sequence and are internally communicated with each other, and the other end of the smearing component is adjacent to the top surface of the joint section.

Furthermore, the smearing component is provided with a sinking groove, the inner diameter of the sinking groove is greater than the inner diameter of the rolling hole, the press cover is arranged in the sinking groove.

Furthermore, the inner diameter of the liquid outlet of the rolling rod is smaller than the inner diameter of the rolling rod, thereby forming a fastening edge in the rolling rod, the outer wall of the cock body of the buckle plug is provided with a clasp, the clasp engages with the fastening edge in the rolling rod to prevent slipping of the buckle plug out of the rolling rod.

Furthermore, the smearing component has a cylindrical shape, a drum shape, or a waist shape.

Furthermore, an outside surface of the smearing component is a smooth surface, a surface with bumps, a protruded ridge surface, or a groove surface.

Furthermore, the smearing component is made from metal, ceramic, glass, plastic, rubber, thermoplastic elastomer or cotton planting bar.

Furthermore, the smearing component is made into integration, or can be a combination of a plurality of smearing elements arranged in parallel in an axial direction.

Compared with the current technology, the advantages of the simple structure and the even smearing of the packaging container according to the invention can be achieved by the liquid outlet end of the container component being provided with the rolling rod, the smearing component is rotatable in a radial direction being arranged on the rolling rod, and the smearing component being positioned on the container body in the axial direction by the buckle plug.

DETAILED DESCRIPTION OF THE INVENTION

In order to make the technical problems to be solved by this invention, the technical solutions of the invention, and advantages of the invention be clearer, the present invention will be further described with reference to the accompanying drawings and embodiments. It should be understood that the embodiments described herein are only intended to illustrate but not to limit the invention.

Figure 1:
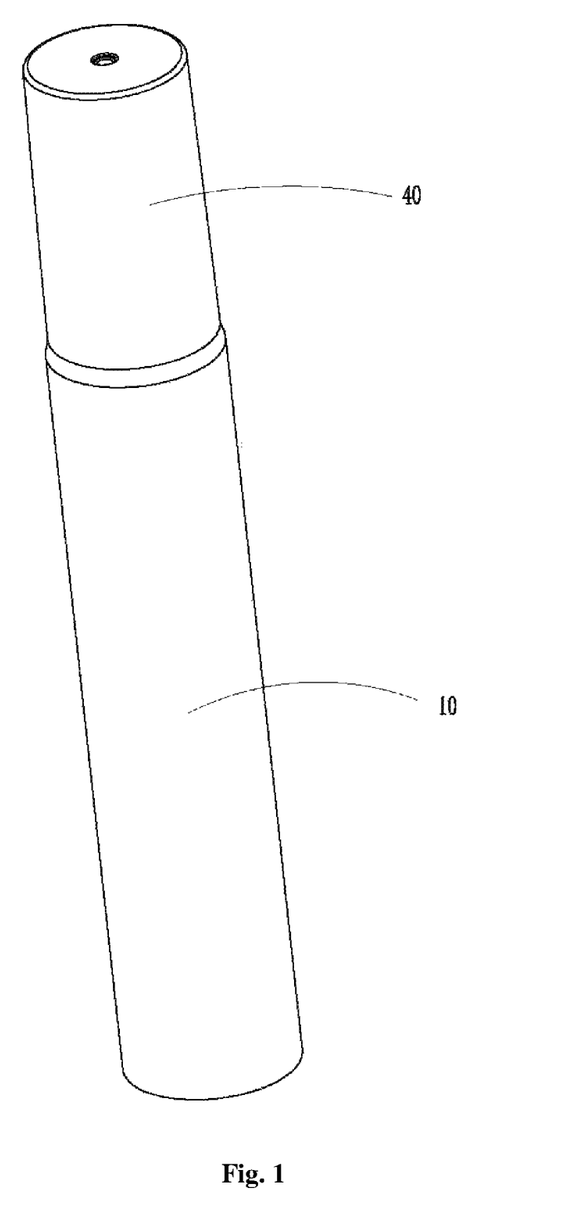
FIG. 1 is a perspective view of a packaging container with a smearing component according to an embodiment of the present invention.
Figure 2:
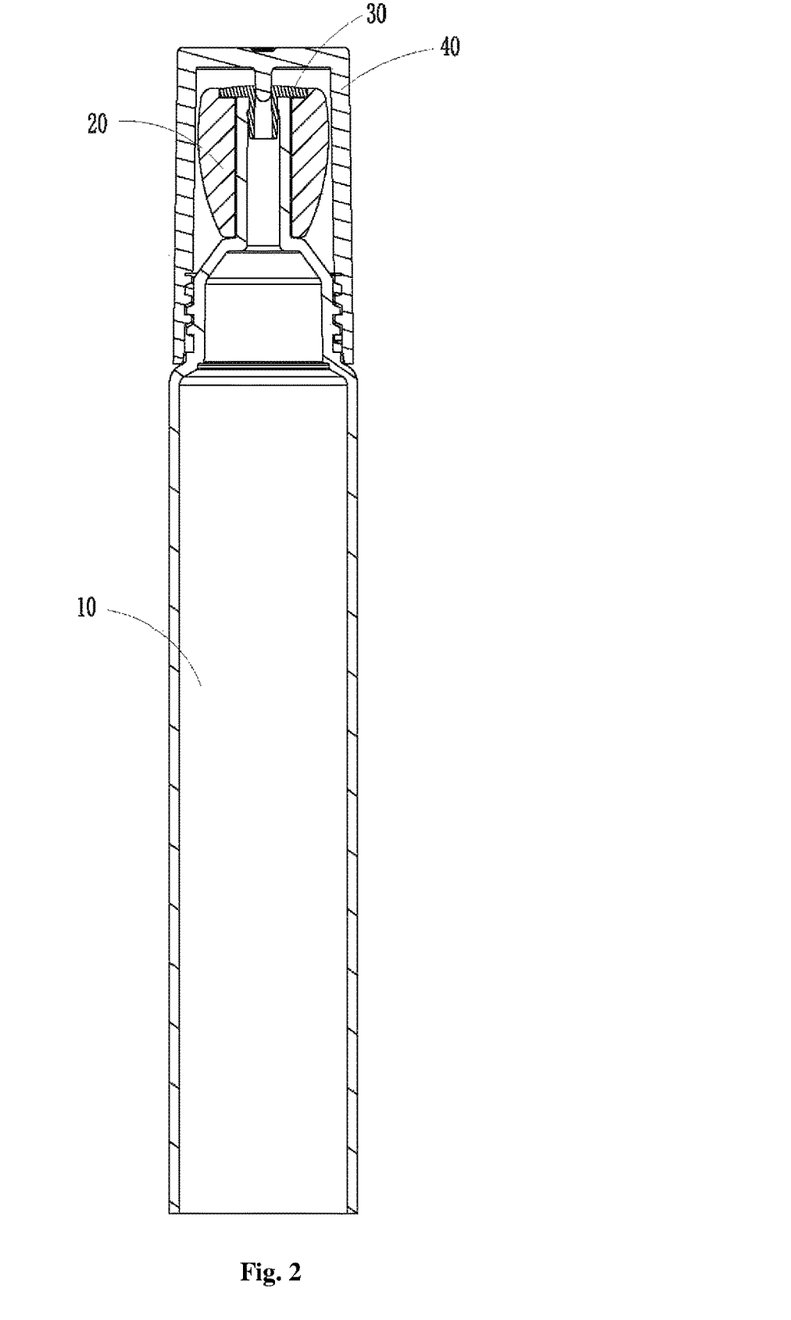
FIG. 2 is a cross-sectional view of the packaging container with the smearing component shown in FIG. 1.
Figure 3:
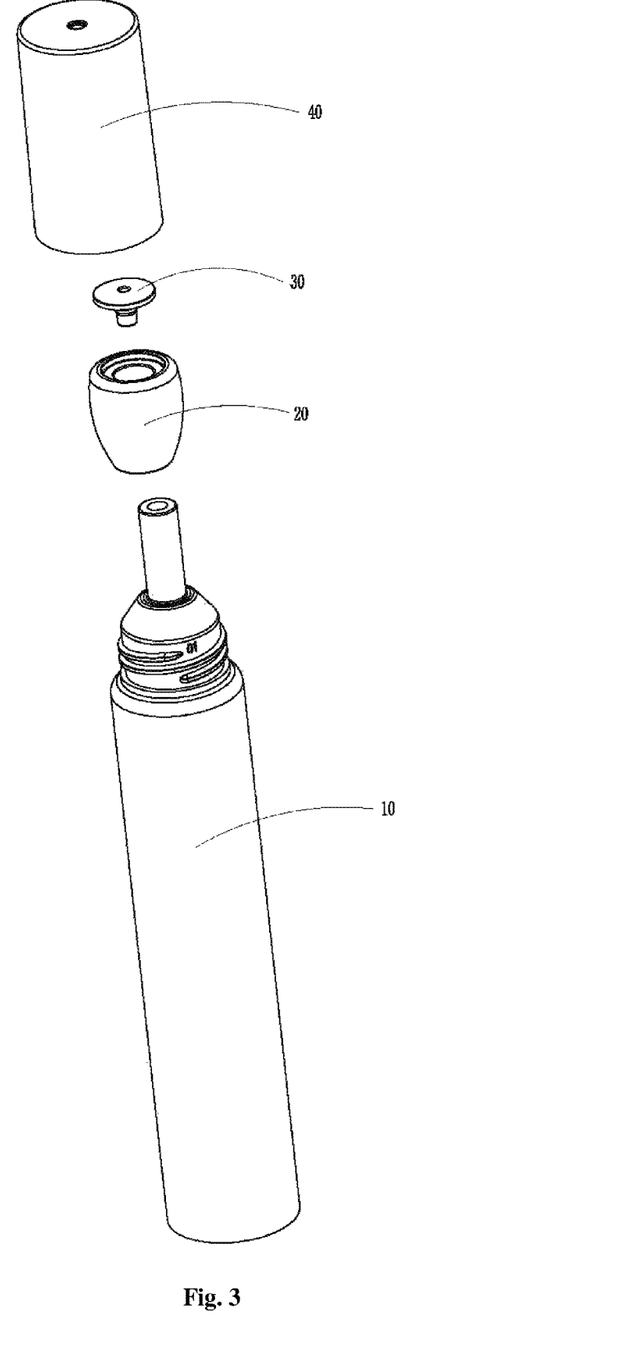
FIG. 3 is an exploded view of the packaging container with the smearing component shown in FIG. 1.

A packaging container with a smearing component according to the present invention is applicable to various medicines, cosmetics and personal care products which need to be smeared. Referring to FIG. 1 to FIG. 3, the packaging container with the smearing component according to the embodiment of the present invention includes a container body 10, a smearing component 20, a buckle plug 30 and a sealing cap 40. The smearing component 20 is rotatably arranged at an opening end of the container body 10, a part of the buckle plug 30 is extended into and fixed in the container body 10, another part of the buckle plug 30 matches with an end of the smearing component 20 and combines with the container body 10 to position the smearing component 20 on the container body 10 in an axial direction, it should be noticed that the buckle plug also can be fixed on the container body by any other available means such as adhesives which can used for fixing the buckle plug with the container body together, the sealing cap 40 matches with an end of the container body 10 thus to seal the container body 10.

Figure 4:
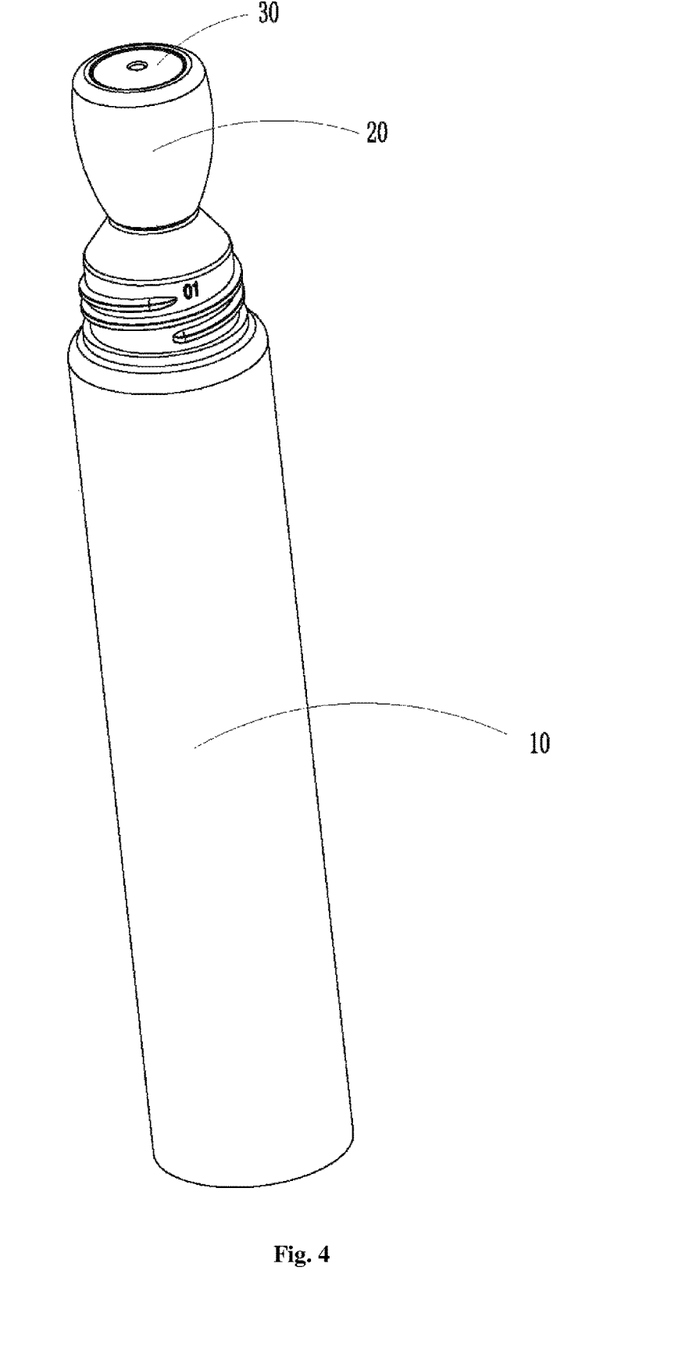
FIG. 4 is a perspective view of the packaging container with the smearing component shown in FIG. 1, wherein the sealing cap of the packaging container is opened.
Figure 5:
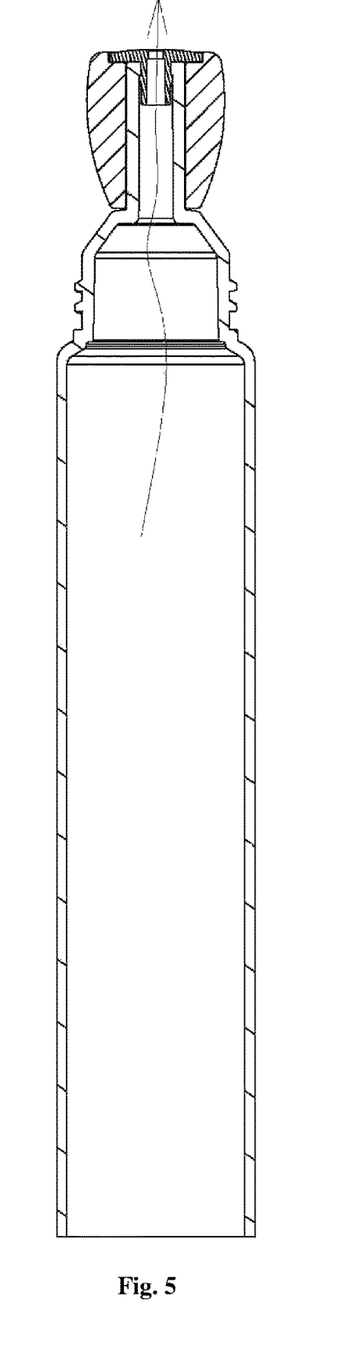
FIG. 5 is a cross-sectional view of the packaging container with the smearing component shown in FIG. 4, wherein the sealing cap of the packaging container is opened.
Figure 6:
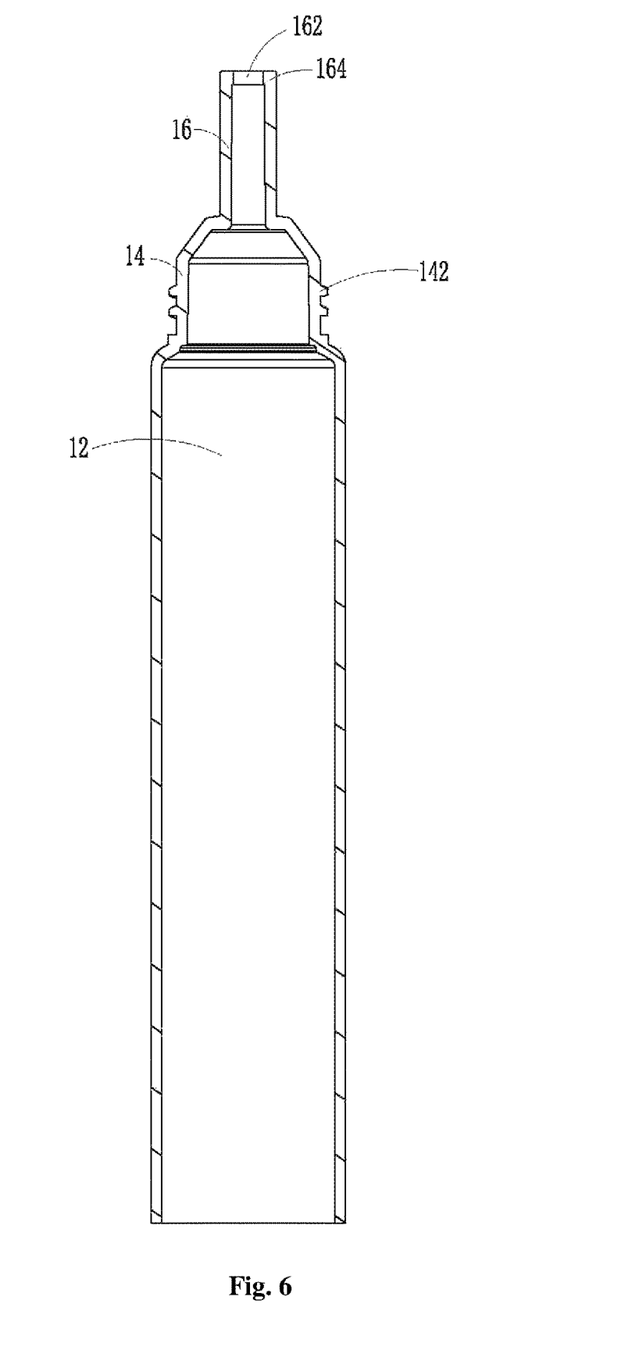
FIG. 6 is a cross-sectional view of a container body of the packaging container with the smearing component shown in FIG. 1.

Referring to FIG. 4 to FIG. 6, the container body 10, for example, may be a plastic tube, a plastic aluminum tube, a bottle, a jar or any other container, the container body 10 includes a receiving section 12, a joint section 14 and a rolling rod 16, the receiving section 12, the joint section 14 and the rolling rod 16 are arranged in sequence and internally communicated with each other. The rolling rod 16 may be formed integrally with the container body, also, it may be a separate part fixed on the container body. Preferably, the receiving section 12, the joint section 14 and the rolling rod 16 have the same axle line, and the radially sizes of the receiving section 12, the joint section 14 and the rolling rod 16 decrease gradually. The receiving section 12 is used for containing objects. The joint section 14 connects with the receiving section 12 to and the rolling rod 16, and the end of the joint section 14 adjacent to the receiving section 12 is provided with external thread 142 which used for engaging with the sealing cap 40. The rolling rod 16 is cylindrical in shape, it is used as a rolling shaft convenient for rolling smearing operation of the smearing component 20. An end of the rolling rod 16 far away from the joint section 14 is provided with a liquid outlet 162 for discharging liquid. The inner diameter of the liquid outlet 162 is smaller than the inner diameter of the rolling rod, thereby forming a fastening edge 164, the fastening edge 164 engages with the buckle plug 30 to fasten the buckle plug 30 on the rolling rod 16.

Figure 7:
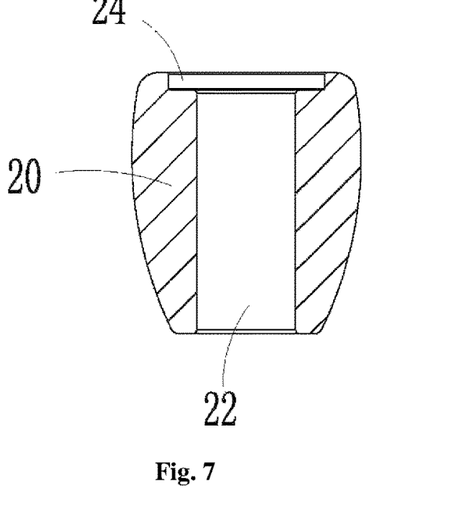
FIG. 7 is a cross-sectional view of the smearing component of the packaging container with the smearing component shown in FIG. 1.

For the smearing component 20, please refer to FIG. 7, the inside of the smearing component 20 is provided with a rolling hole 22, the smearing component 20 is arranged around the rolling rod 16 by the matching of the rolling hole 22 and the rolling rod 16, and the rolling rod 16 serves as a rolling shaft during the rotation of the smearing component. In this embodiment, an end of the smearing component 20 is arranged near to a top surface of the joint section 14, the end surface of another end of the smearing component 20 is provided with a sinking groove 24, the inner diameter of the sinking groove 24 is greater than the inner diameter of the rolling hole 22. The sinking groove 24 engages with the buckle plug 30, thus the buckle plug 30 can prevent the smearing component 20 from slipping out of the rolling rod 16. The smearing component 20 may have a cylindrical shape, a drum shape, a waist shape and the like, the outside surface of the smearing component 20 may be a smooth smearing surface, also it may be a non-smooth smearing surface with bumps, protruded ridges or grooves having massaging effects. Preferably, the smearing component 20 may be made from metal, ceramic or glass, thus the smearing component 20 can absorb heat, the user can have cool experiences. The smearing component 20 also can be made from plastic, rubber, thermoplastic elastomer or cotton planting bar, so that it can be soft and can achieve comfortable massage effects.

Figure 8:
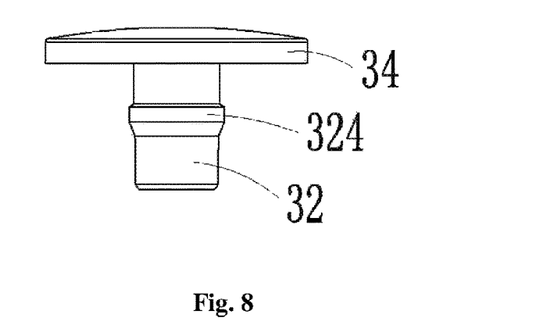
FIG. 8 is an enlarged side view of a buckle plug of the packaging container with the smearing component shown in FIG. 1.
Figure 9:
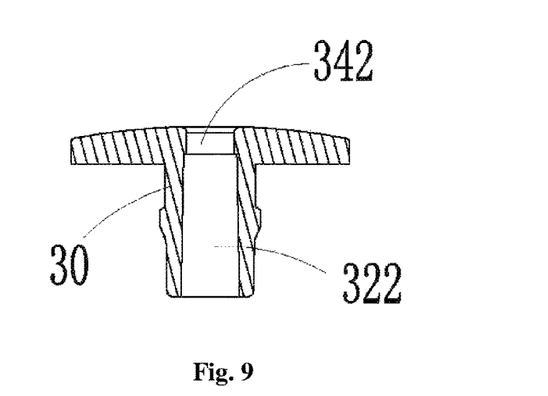
FIG. 9 is an enlarged cross-sectional view of the buckle plug shown in FIG. 8.

Please refer to FIG. 8 and FIG. 9, the buckle plug 30 includes a cock body 32 and a press cover 34 which are molding together integrally, the cock body 32 extends from the middle of a side of the cover 34. The shape and size of the cock body 32 match with the shape and size of the liquid outlet 162 of the rolling rod 16, so that the sealing between the buckle plug 30 and rolling rod 16 can be achieved, the inside of the cock body 32 is provided with a through-hole 322 in an axial direction, the outer wall of the cock body 32 is provided with a clasp 324, the clasp 324 engages with fastening edge 164 in the rolling rod 16 to prevent the slipping of the buckle plug 30 out of the rolling rod 16. In practice, the rolling rod 16 and the buckle plug 30 may be fastened by any available matching modes depending on circumstances, such as adhesives and threads and the like. The middle of the cover 34 is provided with an opening 342, the opening 342 can communicate with the through-hole 322 of the cock body 32, thereby forming a channel for discharging liquid between the container body 10 and outside. Please refer to FIG. 2 and FIG. 5, the press cover 34 is arranged in the sinking groove 24 of the smearing component 20, thereby preventing the axial movement of the smearing component 20 on the rolling rod 16 and the slipping of the smearing component 20 out of the rolling rod 16. In particular, the smearing component 20 may be not provided with the sinking groove 24 if the cover 34 of the buckle plug 30 can prevent the slipping of the smearing component 20 out of the rolling rod 16.

Figure 10:
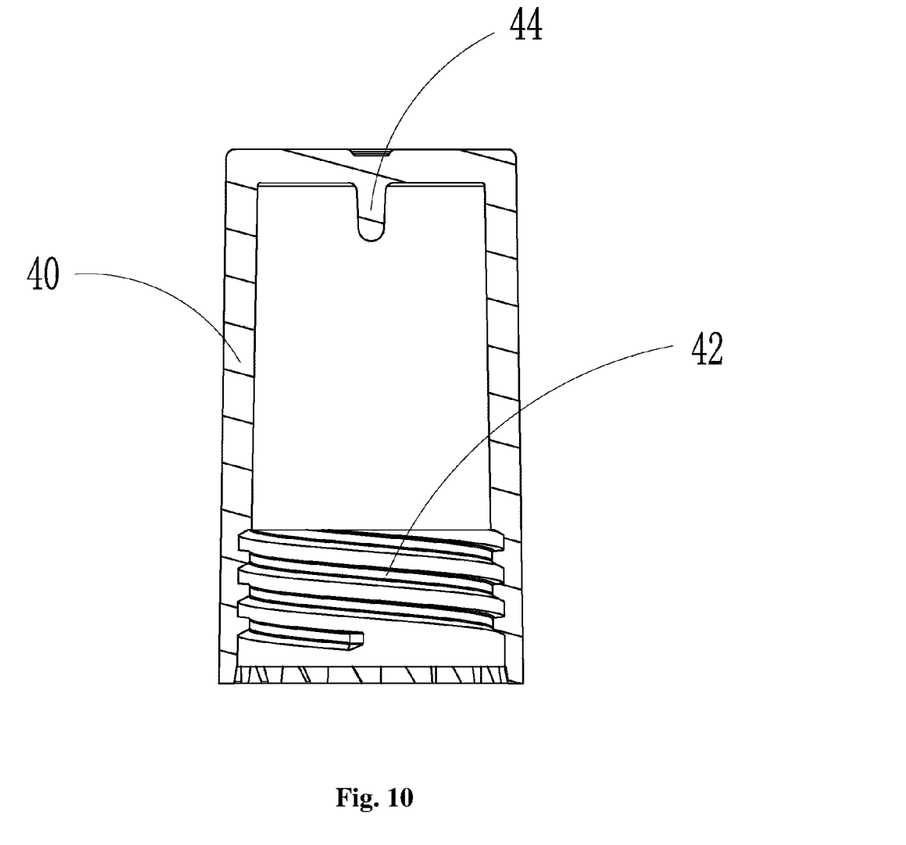
FIG. 10 is a cross-sectional view of the sealing cap of the packaging container with the smearing component shown in FIG. 1.

Please refer to FIG. 10, one end of the sealing cap 40 is closed, the other end is opened, the inner wall of the opened end is provided with internal thread 42, the closed end is inwardly provided with a sealing plunger 44 in an axial direction. The internal thread 42 of the sealing cap 40 engages with the external thread 142 of the joint section 14, the sealing cap may be fixed on the container body 10, thus the sealing cap 40 can cover the joint section 14, the smearing component 20 on the rolling rod 16, and the buckle plug. After the sealing cap 40 is engaged with the container body 10, the sealing plunger 44 is inserted into the opening 342 of the press cover 34, so that the container body 10 can be entirely sealed, and is resistant to dust.

It should be noted that the smearing component 20 can be made integrally, alternatively it can be a combination of a plurality of smearing elements arranged in parallel in an axial direction.

The advantages of the simple structure and the even smearing of the packaging container according to the invention can be achieved by the liquid outlet end of the container body being provided with the rolling rod 16, the smearing component 20 rotatable in a radial direction being arranged on the rolling rod 16, and the smearing component 20 being positioned between the cover 34 and the joint section 14 in the axial direction by the buckle plug 30. In addition, the smearing component 20 also may be made from material with heat-absorbing action, so that human skin can have cool experiences, the smearing component 20 can be made from plastic, rubber, thermoplastic elastomer or cotton planting bar, so that the smearing component 20 is soft and can achieve comfortable massage effects.

The present invention has been further detailed in the above descriptions with reference to the preferred embodiments; however, it shall not be construed that implementations of the present invention are only limited to these descriptions. Many simple deductions or replacements may further be made by those of ordinary skill in the art without departing from the conception of the present invention, and all of the deductions or replacements shall be considered to be covered within the protection scope of the present invention.

The invention claimed is:

1. A packaging container with a smearing component comprising a container body, a smearing component having a smearing surface, and a sealing cap, wherein the container body comprises a rolling rod, the rolling rod is cylindrical in shape, a free axial end of the rolling rod is provided with a liquid outlet internally communicated with the container body, an inside of the smearing component is provided with a rolling hole, the smearing component is rotatably arranged around the rolling rod by matching of the rolling hole and the rolling rod, the sealing cap is engaged with the rolling rod of the container body and the container body is entirely sealed by the sealing cap, wherein the packaging container further comprises a buckle plug, the buckle plug is fixed on the free axial end of the rolling rod of the container body, and a part of the buckle plug matches with an end of the smearing component, and the smearing component is positioned in an axial direction by the buckle plug and the container body, wherein the buckle plug is provided with a channel communicating with the liquid outlet of the rolling rod for discharging liquid from the container body.

2. The packaging container of claim 1, wherein the buckle plug comprises a cock body and a cover, the cock body is extended into the liquid outlet of the rolling rod and engages with the rolling rod, the cover engages with an end of the smearing component to prevent movement of the smearing component on the rolling rod in an axial direction.

3. The packaging container of claim 2, wherein the smearing component is provided with a sinking groove, the inner diameter of the sinking groove is greater than the inner diameter of the rolling hole, and the cover is arranged in the sinking groove.

4. The packaging container of claim 2, wherein the inner diameter of the liquid outlet of the rolling rod is smaller than the inner diameter of the rolling rod, thereby forming a fastening edge in the rolling rod, an outer wall of the cock body of the buckle plug is provided with a clasp, the clasp engages with the fastening edge in the rolling rod to prevent slipping of the buckle plug out of the rolling rod.

5. The packaging container of claim 2, the channel comprises a through-hole in the cock body in an axial direction and an opening provided at the middle of the cover, the opening communicates with the through-hole of the cock body.

6. The packaging container of claim 1, wherein the container body further comprises a receiving section and a joint section, the receiving section, the joint section and the rolling rod are arranged in sequence and are internally communicated with each other, an other end of the smearing component is adjacent to a top surface of the joint section.

7. The packaging container of claim 1, wherein the smearing component has a cylindrical shape, a drum shape, or a waist shape.

8. The packaging container of claim 1, wherein an outside surface of the smearing component is a smooth surface, or a surface with bumps, protruded ridges or grooves.

9. The packaging container of claim 1, wherein the smearing component is made from metal, ceramic, glass, plastic, rubber, thermoplastic elastomer or cotton planting bar.

10. The packaging container of claim 1, wherein the smearing component is made into integration or a combination of a plurality of smearing elements arranged in parallel in an axial direction.

11. A packaging container with a smearing component comprising a container body, a smearing component having a smearing surface, and a sealing cap, the sealing cap engaging with the container body and the container body being entirely sealed by the sealing cap, wherein the packaging container further comprises a buckle plug, the smearing component is arranged around an opening end of the container body and capable of rotating relative to the container body freely, a part of the buckle plug is fixed on the container body, an other part of the buckle plug matches with an end of the smearing component, and the smearing component is axially positioned by the buckle plug and the container body, wherein the opening end of the container body comprises a rolling rod, the rolling rod is cylindrical in shape, a free end of the rolling rod is provided with a liquid outlet internally communicated with the container body, an inside of the smearing component is provided with a rolling hole, the smearing component is arranged around the rolling rod by matching of the rolling hole and the rolling rod, the buckle plug comprises a cock body and a cover, the cock body is extended into the liquid outlet of the rolling rod and engages with the rolling rod, the cover engages with an end of the smearing component to prevent movement of the smearing component on the rolling rod in an axial direction.

12. The packaging container of claim 11, wherein the buckle plug is provided with a channel for discharging liquid from the container body, the channel comprises a through-hole in the cock body in an axial direction and an opening provided at the middle of the cover, the opening communicates with the through-hole of the cock body.

13. The packaging container of claim 11, wherein the container body further comprises a receiving section and a joint section, the receiving section, the joint section and the rolling rod are arranged in sequence and are internally communicated with each other, an other end of the smearing component is adjacent to a top surface of the joint section.

14. The packaging container of claim 11, wherein the smearing component is provided with a sinking groove, the inner diameter of the sinking groove is greater than the inner diameter of the rolling hole, and the cover is arranged in the sinking groove.

15. The packaging container of claim 11, wherein the inner diameter of the liquid outlet of the rolling rod is smaller than the inner diameter of the rolling rod, thereby forming a fastening edge in the rolling rod, an outer wall of the cock body of the buckle plug is provided with a clasp, the clasp engages with the fastening edge in the rolling rod to prevent slipping of the buckle plug out of the rolling rod.

16. The packaging container of claim 11, wherein the smearing component has a cylindrical shape, a drum shape, or a waist shape.

17. The packaging container of claim 11, wherein an outside surface of the smearing component is a smooth surface, or a surface with bumps, protruded ridges or grooves.

18. The packaging container of claim 11, wherein the smearing component is made from metal, ceramic, glass, plastic, rubber, thermoplastic elastomer or cotton planting bar.

19. The packaging container of claim 11, wherein the smearing component is made into integration or a combination of a plurality of smearing elements arranged in parallel in an axial direction.

* * * * *